US006546291B2

(12) United States Patent
Merfeld et al.

(10) Patent No.: US 6,546,291 B2
(45) Date of Patent: Apr. 8, 2003

(54) BALANCE PROSTHESIS

(75) Inventors: Daniel M. Merfeld, Lincoln, MA (US); Steven D. Rauch, Watertown, MA (US); Conrad Wall, III, Boston, MA (US); Marc Weinberg, Needham, MA (US)

(73) Assignees: Massachusetts Eye & Ear Infirmary, Boston, MA (US); Charles Stark Draper Laboratory, Cambridge, MA (US)

( * ) Notice: Subject to any disclaimer, the term of this patent is extended or adjusted under 35 U.S.C. 154(b) by 0 days.

(21) Appl. No.: 09/785,803

(22) Filed: Feb. 16, 2001

(65) Prior Publication Data

US 2002/0010497 A1 Jan. 24, 2002

Related U.S. Application Data

(60) Provisional application No. 60/183,008, filed on Feb. 16, 2000.

(51) Int. Cl.$^7$ ................................................. A61N 1/08
(52) U.S. Cl. ........................................................ 607/62
(58) Field of Search .............................. 607/48, 49, 62; 600/595

(56) References Cited

U.S. PATENT DOCUMENTS

| 5,919,149 A | 7/1999 | Allum ........................ 600/595 |
| 6,063,046 A | 5/2000 | Allum ........................ 600/595 |
| 6,219,578 B1 | 4/2001 | Collins et al. |

OTHER PUBLICATIONS

"Vestibular Function and Anatomy" by C. Wall III and J. T. Vrabec, Department of Otolaryngology–Head and Neck Surgery, University of Texas Medical Branch, Galveston, TX, pp. 1891–1901.

"Prototype Neural Semicircular Canal Prosthesis Using Patterned Electrical Stimulation" by W. Gong and D. M. Merfeld, Annals of Biomedical Engineering, vol. 28, pp. 572–581, 2000.

*Primary Examiner*—Scott M. Getzow
(74) *Attorney, Agent, or Firm*—Fish & Richardson P.C.

(57) ABSTRACT

A wearable balance prosthesis provides a information indicative of a wearer's spatial orientation. The balance prosthesis includes an motion sensing system to be worn by the wearer and a signal processor in communication with the motion sensing system. The signal processor provides an orientation signal to an encoder. The encoder generates a feedback signal on the basis of the estimate of the spatial orientation provides that signal to a stimulator coupled to the wearer's nervous system.

17 Claims, 11 Drawing Sheets

BALANCE PROSTHESIS

RELATED APPLICATIONS

This application claims priority from U.S. Provisional Application 60/183,008, filed on Feb. 16, 2000, the contents of which are herein incorporated by reference.

FIELD OF INVENTION

This invention relates to sensory prostheses, and in particular, to a prosthesis for ameliorating the symptoms of balance or vestibular disorders.

BACKGROUND

In order to stand erect, one constantly makes minor adjustments to avoid falling over. These minor adjustments involve the often subtle contraction and relaxation of a large number muscles. The choice of which muscles to contract and how hard to contract them depends on one's perception of spatial orientation. The vestibular system contributes substantially to one's perception of spatial orientation.

The standing human being is thus a feedback control system in which the vestibular system provides motion signals to the brain. Without these motion signals, the feedback control system rapidly becomes unstable. This instability is manifested in general clumsiness, frequent collisions, and spontaneous falls. Among the elderly, such falls account for over half of all accidental deaths.

Persons with improperly functioning balance systems can also experience difficulty compensating for head motion when attempting to gaze in a particular direction. This results in such symptoms as blurred vision while walking, or the inability to read when in a moving vehicle.

A person whose lack of vestibular function affects primarily balance can compensate by using a cane or walker. However, these devices require the use of one or both hands. In addition, these devices do not attempt to replace the sense of balance. Instead, they merely reduce the likelihood of injury that arises from loss of one's sense of balance.

At present, a person whose lack of vestibular function results in an inability to gaze in a selected direction has little choice but to endure the condition.

SUMMARY

The invention provides a balance prosthesis that is small enough and light enough to be worn in the course of one's daily activities. Such a balance prosthesis provides the wearer information indicative of the spatial orientation of a body part (most commonly the head) of the wearer.

As used herein, the term "wearer" refers to any animal that wears the balance prosthesis and receives information therefore. The wearer can be a human under a doctor's care or any other animal. The wearer need not have a balance disorder. For example, the wearer of the balance prosthesis can be a human or animal research subject. Alternatively, the wearer can be a human or animal seeking sensory enhancement provided by the balance prosthesis.

The balance prosthesis includes a motion sensing system to be worn on the body part whose orientation is sought. The motion sensing system generates a motion signal indicative of motion experienced by that body part. The motion signal is then passed to a signal processor, which generates an estimate of the spatial orientation of the body part on the basis of the motion signal.

The balance prosthesis also includes an encoder in communication with the signal processor. The encoder generates a feedback signal on the basis of the estimate of the spatial orientation. This feedback signal is provided to a stimulator configured to provide a signal to the nervous system in response to the feedback signal.

In one embodiment, the stimulator includes a tactor set that includes one or more tactors adapted to be worn against skin of the wearer. The feedback signal causes one or more of these tactors to vibrate, in response to a control signal from the encoder.

A variety of modulation methods are available to the encoder for communicating spatial orientation to the wearer. In one aspect of the invention, the encoder pulses a selected tactor at a pulse repetition frequency indicative of the spatial orientation. In another aspect of the invention, the encoder is configured to select a subset of the tactor set on the basis of spatial orientation and to excite only the tactors in that subset. In yet another aspect of the invention, the encoder is configured to sequentially excite a plurality of subsets of the tactor set according to an excitation sequence. The plurality of subsets and the excitation sequence are selected on the basis of the spatial orientation.

In another embodiment of the invention, the stimulator is an electrode in communication with the encoder. The electrode is adapted to be inserted proximate to a nerve in the wearer and to carry a signal indicative of the spatial orientation. Again, a variety of modulation methods are available for communicating spatial orientation to the wearer. In one aspect of the invention, the encoder is configured to apply a sequence of pulses to the electrode at a pulse repetition frequency indicative of the spatial orientation. In another aspect of the invention, the encoder is configured to energize the electrode with an energizing amplitude selected on the basis of the spatial orientation.

In another embodiment, the encoder provides a feedback signal that depends not only on the spatial orientation of the wearer's body part but also on the activity in the wearer's nervous system, This embodiment includes a measurement electrode in communication with the encoder and adapted for placement in communication with a nerve. The measurement electrode detects an endogenous signal in the nerve and provides the information in that endogenous signal to the encoder. The encoder then generates a feedback signal on the basis of the both the information contained in the endogenous signal and the estimate of the spatial orientation provided by the digital signal processor.

Other stimulators can be substituted or used in addition to those described above. For example, the stimulator can provide an acoustic signal to the wearer. Alternatively, the stimulator can provide a visual signal. Such a stimulator can be incorporated into a pair of glasses.

One or more additional signals can be provided to the encoder for use in generating a feedback signal. For example, in some cases, it is useful to provide a feedback signal that depends not only on the spatial orientation of one body part but on the spatial orientation of additional body parts of the wearer. In this embodiment, the balance prosthesis includes an additional motion sensing system to be worn on an additional body part of the wearer. The additional motion sensing system generates an additional motion signal indicative of motion experienced by the additional body part of the wearer. The balance prosthesis also includes an additional signal processor in communication with the additional motion sensing system and the encoder. The additional signal processor is configured to generate an estimate of the spatial orientation of the additional body part on the basis of the additional motion signal and to provide that estimate to the encoder.

Other types of additional signals can be provided to the encoder for use in generating a feedback signal. For example, the additional signal can be one that indicates the location of the wearer relative to an external coordinate system. The additional signal can also indicate other properties associated with one or more body parts, such as joint angles of various joints. The additional signal can also provide information indicative of tactile pressure experienced by the wearer.

The motion sensing system can include at least one rotation sensor. Typically, the rotation sensor is a micro-mechanical device having a proof mass that undergoes a periodic motion susceptible to disturbance by a rotation. An example of such a micro-mechanical device is a tuning fork gyroscope.

The motion sensing system can also include at least one translation sensor. Typically, the translation sensor is a micro-mechanical device having a proof mass. The proof mass has a position that deviates from an equilibrium position in response to a linear acceleration.

In one embodiment of the balance prosthesis, the signal processing system includes a low-pass filter to filter a first inertial guidance signal and a high-pass filter to filter a second inertial guidance signal. The low-pass filter and the high-pass filter have complementary filter transfer functions.

In another embodiment of the balance prosthesis, the signal processing system is configured to distinguish linear acceleration due to gravity from linear acceleration resulting in translation. The signal processing system can achieve this by determining a current direction of a gravity vector on the basis of an integrated rotation sensor output. Having determined this direction, the signal processing system can then remove the effect of the gravity vector from a translation sensor output.

These and other features and advantages of the invention will be apparent from the following detailed description, and the figures, in which:

DETAILED DESCRIPTION

Figure 1:
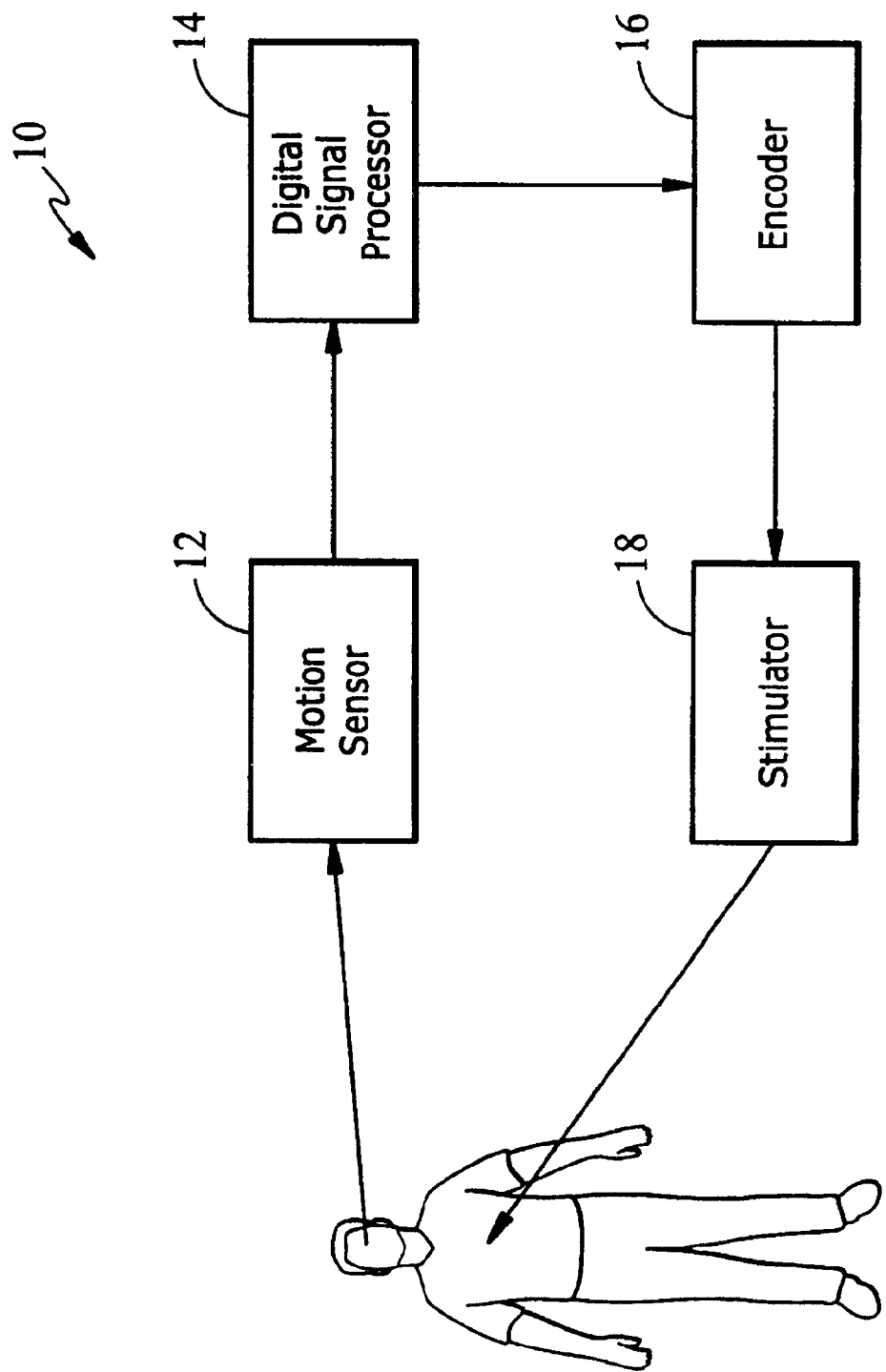
FIG. 1 is a block diagram of the balance prosthesis.

The invention provides a portable balance prosthesis that can be worn in the course of daily activities. The balance prosthesis 10, shown schematically in FIG. 1, includes an motion sensing system 12 having an output that depends on rotational and translational motion experienced by the wearer. The output from the motion sensing system 12 is provided to a digital signal processor 14 that provides real-time estimates of the wearer's orientation and velocity in three-dimensional space. These estimates are then provided to an encoder 16 that drives a stimulator 18 in communication with the wearer's nervous system. The encoder 16 translates the real-time estimates of the wearer's orientation and velocity into a form that can be used by the wearer.

Figure 2:
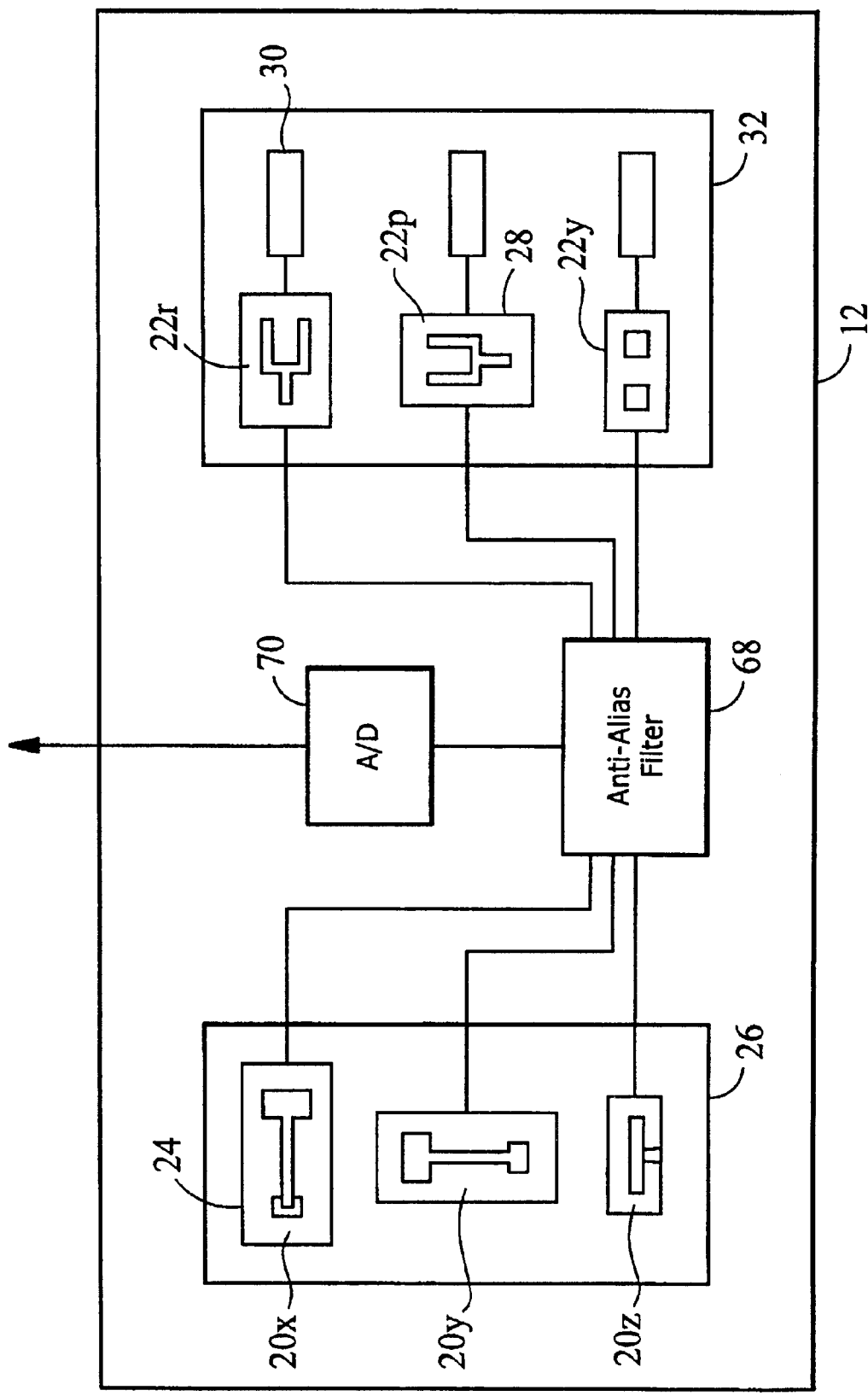
FIG. 2 is a schematic representation of a motion sensing system for the balance prosthesis of FIG. 1.

The motion sensing system 12, shown in more detail in FIG. 2, includes both translation sensors 20 for sensing translation of the wearer and rotation sensors 22 for sensing rotation of the wearer. Preferably, there are three translation sensors 20x, 20y, 20z oriented to sense the wearer's translation along three coordinate axes and three rotation sensors 22r, 22p, 22y oriented to sense the wearer's roll, pitch and yaw. In one embodiment of the prosthesis, each of the three translation sensors 20 is hermetically sealed in a nitrogen filled leadless ceramic chip carrier ("LCCC") 24. The LCCCs 24 are combined into a multi-chip module ("MCM") 26 having a volume on the order of 0.35 cubic inches. Each of the three rotation sensors 22 is encased in an evacuated LCCC 28 approximately 0.25 inch on a side and 0.1 inch thick. The evacuated LCCC 28 and an application specific integrated circuit 30 ("ASIC") for driving the rotation sensor 22 are mated in a multi-chip module ("MCM") 32 that is densely packed to reduce its volume and to enhance its structural rigidity. The volume of an MCM 32 containing all three rotation sensors 22 and their associated ASICs 30 is on the order of 0.47 cubic inches.

Figure 3:
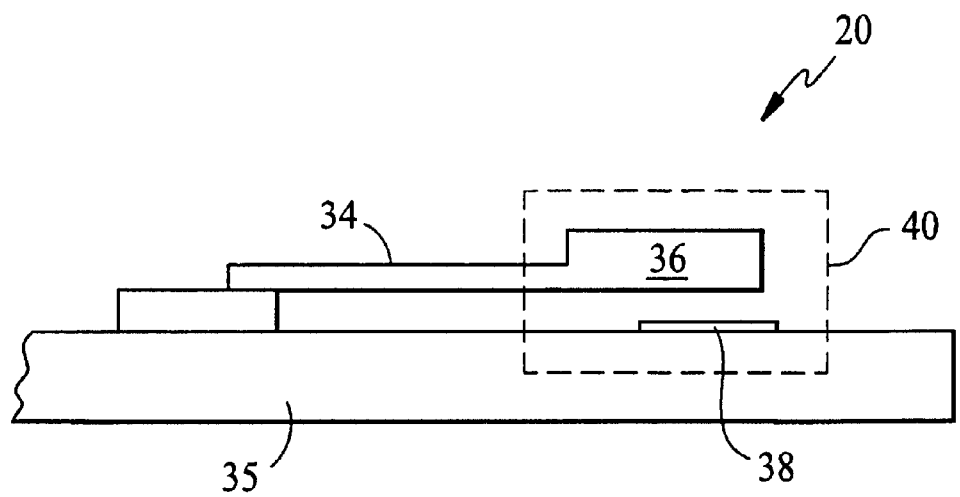
FIG. 3 is a translation sensor from the motion sensing system of FIG. 2.

In the embodiment shown in FIG. 3, each translation sensor 20 is a micro-mechanical device in which a cantilevered beam 34 is mounted on a substrate 35. The cantilevered beam 34 suspends a proof mass 36 above a sense electrode 38. The proof mass 36 and the sense electrode 38 together form a capacitor 40 having a capacitance that depends in part on the gap separating the proof mass 36 from the sense electrode 38. An acceleration normal to the substrate 35 results in a force that deflects the proof mass 36 toward or away from the sense electrode 38, thereby changing the capacitance. This change in capacitance modulates a signal, which thus carries information indicative of acceleration normal to the cantilevered beam 34.

Figure 4:
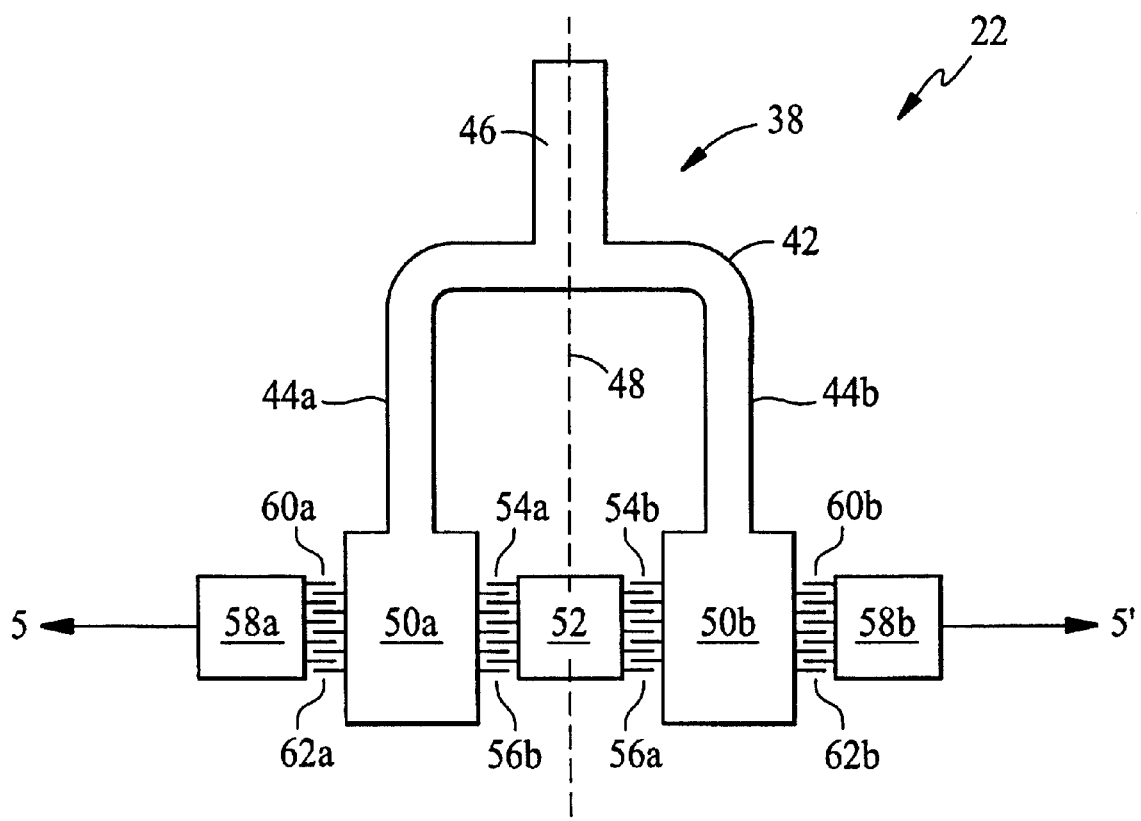
FIG. 4 is a plan view of a rotation sensor from the motion sensing system of FIG. 2.

A typical rotation sensor 22, shown in FIG. 4, is a micro-mechanical device that includes a tuning fork 42 having first and second parallel tines 44a, 44b connected to a base 46. The moving elements of the rotation sensor 22 are typically boron-doped, crystalline silicon anodically bonded to a glass substrate. Such a device, often referred to as a "tuning fork gyroscope," is described in detail in Bernstein et al., U.S. Pat. No. 5,349,855, the contents of which are herein incorporated by reference.

A line extending through the base 46 and parallel to the first and second tines 44a, 44b defines a central axis 48 of the tuning fork 42. The first and second tines 44a, 44b of the tuning fork 42, when the tuning fork 42 is in its equilibrium position, define an equilibrium plane. First and second proof masses 50a, 50b are integrated onto the ends of the first and second tines 44a, 44b respectively.

The rotation sensor 22 also includes an inner comb 52 disposed between the first and second proof masses 50a, 50b. The inner comb has two sets of teeth 54a, 54b, each of which extends away from the central axis 48 in the equilibrium plane. Each proof mass 50a, 50b includes a plurality of inner teeth 56a, 56b extending toward the central axis in the equilibrium plane. These inner teeth 56a, 56b interdigitate with the corresponding teeth 54a, 54b extending from the inner comb 52.

The rotation sensor 22 also includes two outer combs 58a, 58b, each disposed adjacent to a proof mass 50a, 50b. Each outer comb 58a, 58b has a plurality of teeth 60a, 60b extending inwardly toward the central axis 48 in the equilibrium plane. Each proof mass 50a, 50b includes a plurality of outer teeth 62a, 62b that extend away from the central axis 48 in the equilibrium plane. These outer teeth 62a, 62b interdigitate with the corresponding teeth 60a, 60b on the outer combs 58a, 58b.

Figure 5:
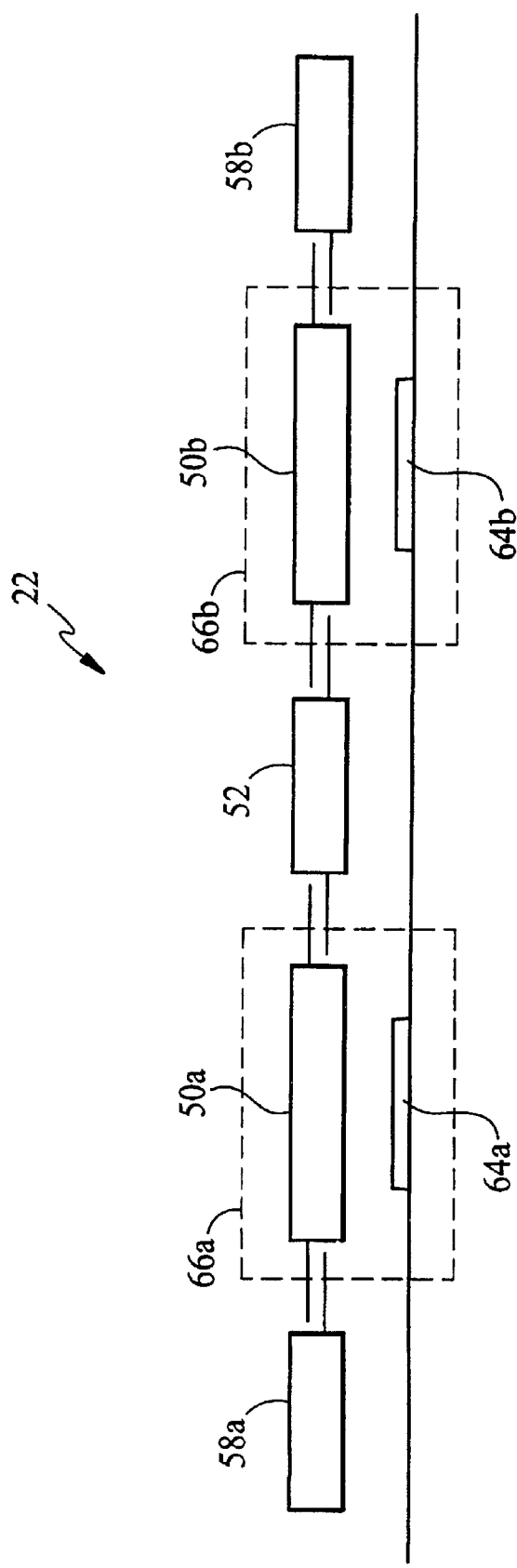
FIG. 5 is a cross-sectional view of the rotation sensor of FIG. 4.

The proof masses 50a, 50b are suspended above first and second sense electrodes 64a, 64b, as shown in the cross-section of FIG. 5. Each proof mass 50a, 50b and its corresponding sense electrode 64a, 64b thus defines a capacitor 66a, 66b having a capacitance that depends on the position of the proof mass 50a, 50b relative to the sense electrode 64a, 64b.

The inner and outer combs 52, 58a, 58b are connected to a voltage source that generates a voltage on their respective teeth 54a, 54b, 60a, 60b. This results in the generation of an electrostatic force that deflects the proof masses 50a, 50b in the equilibrium plane. The voltage on the teeth 54a, 54b, 60a, 60b of the inner and outer combs 52, 58a, 58b is selected to cause oscillation of the proof masses 50a, 50b in the equilibrium plane. To maintain oscillation, the rotation sensor consumes approximately 0.2 watts from a 5 volt DC source. The oscillation of the proof masses 50a, 50b results in the generation of an equilibrium angular momentum vector that is perpendicular to the equilibrium plane and an equilibrium capacitance signal measured at the sense electrodes 64a, 64b.

When the wearer experiences an rotation, the angular momentum vector points in a different direction relative to a fixed reference frame associated with the wearer's surroundings. Because angular momentum of the oscillating proof masses 50a, 50b is conserved, a torque is generated that causes the proof masses 50a, 50b to oscillate above and below the equilibrium plane. This causes the angular momentum vector to recover its original direction.

As the proof masses 50a, 50b oscillate above and below the equilibrium plane, the capacitance of the capacitors 66a, 66b changes. This change provides a signal indicative of rotational motion experienced by the rotation sensor 22. The dynamic response of the rotation sensor 22 has a bandwidth between 100 and 1000 Hz and a maximum rate range of 400 degrees per second.

Referring back to FIG. 2, the signals generated by each of the linear and rotation sensors 20, 22 are passed through an anti-aliasing filter 68 and sampled by an A/D converter 70. Based on the estimated 2.5 millisecond minimum deflection time of the cupula of the semicircular canal, the maximum sampling rate for each of the six signals need be no greater than 1 kHz. The resulting six sample streams are then provided to the digital signal processor 14.

Figure 6:
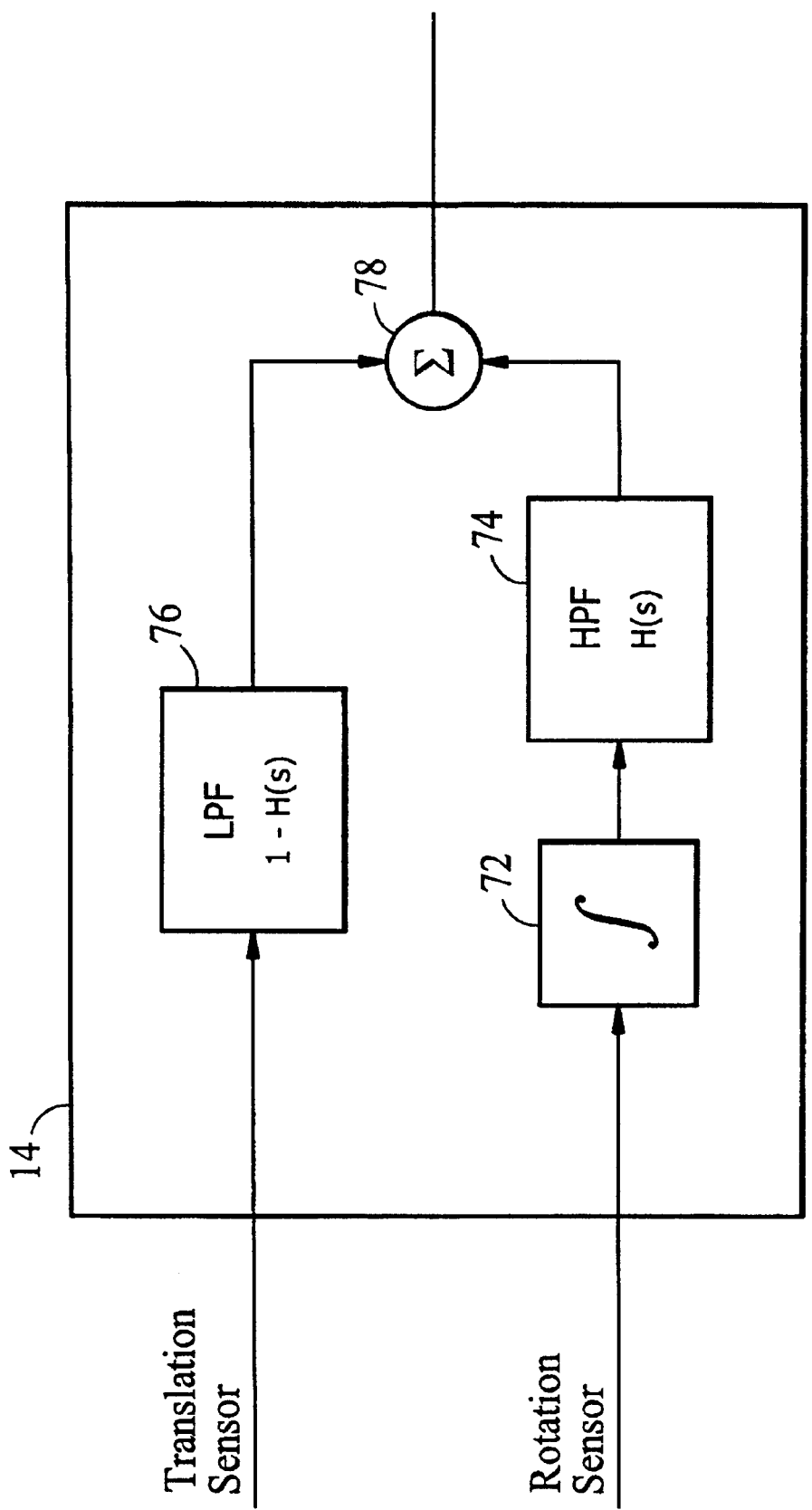
FIG. 6 is a block diagram of one channel of a signal processing system from the balance prosthesis of FIG. 1.

The particular architecture of the digital signal processor 14 will depend on the characteristics of the sensors. In one representative architecture, one channel of which is shown in FIG. 6, sample streams from the rotation sensors 22 are passed through integrators 72 to obtain angular displacements. The outputs of the integrators 72 are then passed through high-pass filters 74 to remove low-frequency errors introduced by variations in the rotation sensors' bias voltages. The signals from the translation sensors 20 are likely to have high-frequency components tainted by contributions resulting from rotational motion. As a result, it is useful to pass the sample streams from the translation sensors 20 through low-pass filters 76. Suitable low-pass filters 76 include third-order Butterworth filters having −3 dB points near 0.03 Hz. To avoid distortion, the transfer functions for the high-pass filters 74 and their corresponding low-pass filters 76 are complementary. The outputs of the high-pass filters 74 and the low-pass filters 76 are then passed through corresponding summers 78 to obtain an estimate of the wearer's orientation in an inertial coordinate system.

The architecture shown in FIG. 6 is typical of one channel of the digital signal processor 14. A typical implementation of the digital signal processor 14 includes one channel for each rotation sensor 22 and one channel for each translation sensor 20.

Figure 7:
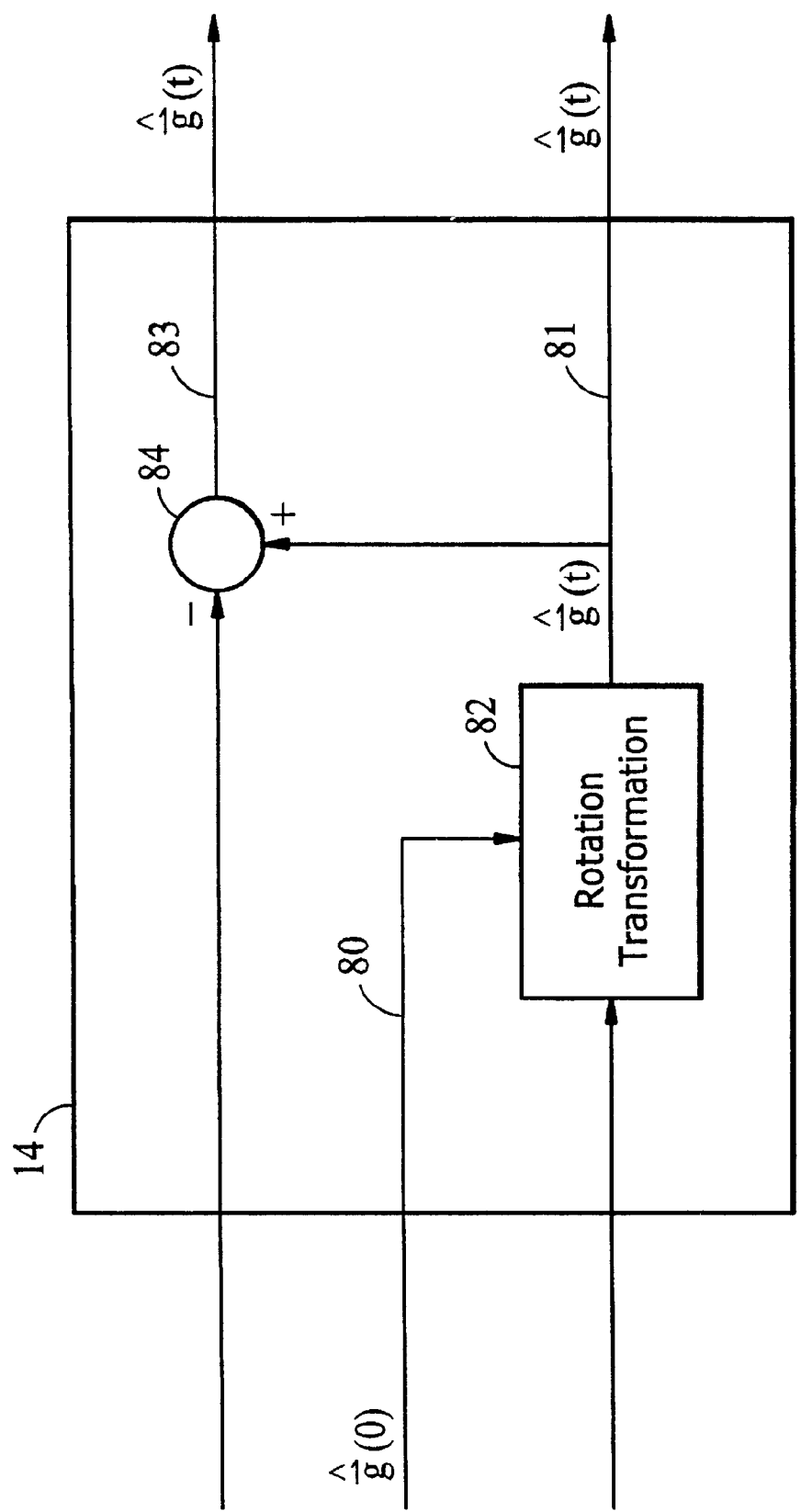
FIG. 7 is a signal block diagram of one channel of the signal processing system of FIG. 6 modified to distinguish gravity from linear acceleration.

By itself, a translation sensor 22 cannot distinguish between an acceleration that results in translation and the omnipresent acceleration due to gravity. The availability of rotational cues enables the digital signal processor 14 to distinguish between these two types of acceleration. As illustrated in FIG. 7, given an initial orientation 80 of the gravity vector and the contributions of a rotation sensor 22, a rotation transformation 82 can provide an estimate of the magnitude and direction of the gravity vector 81 at any instant. This gravity vector 81 can then be provided to a differencing element 84 for combination with the measurement provided by the three linear accelerometers 20 at that instant. The acceleration vector that remains is the linear acceleration vector 83 that results in actual translation of the wearer. This processing thus yields two time-varying signals: a first signal 81 indicating the gravity vector, and a second signal 83 indicating the linear acceleration vector 83.

Other signal processing architectures can be used to estimate the wearer's orientation in an inertial coordinate system. For example, a Kalman filter that incorporates a model of the dynamic characteristics of the motion sensing system 12 and of the wearer can be used to derive such an estimate.

The resulting estimates from the digital signal processor 14 are then provided to the encoder 16 for translation into a feedback signal that can be used to stimulate the wearer's nervous system. In one practice of the invention, the wearer is modeled as an unstable second order system, in which case a feedback signal that the wearer can use to stabilize himself must carry information on both orientation and rate of change of orientation. An example of such a feedback signal is $$y(t) = k1*theta + k2*d(theta)/dt$$

where the constants k1 and k2 can be varied to provide an estimate of the wearer's orientation, the rate of change of that orientation, or a linear combination of the two.

The feedback signal is provided to a stimulator 18 for display to the wearer. As will be apparent from the following embodiments, the term "display" in this context is not limited to visual display but includes any pathway to the wearer's central nervous system.

Figure 15:
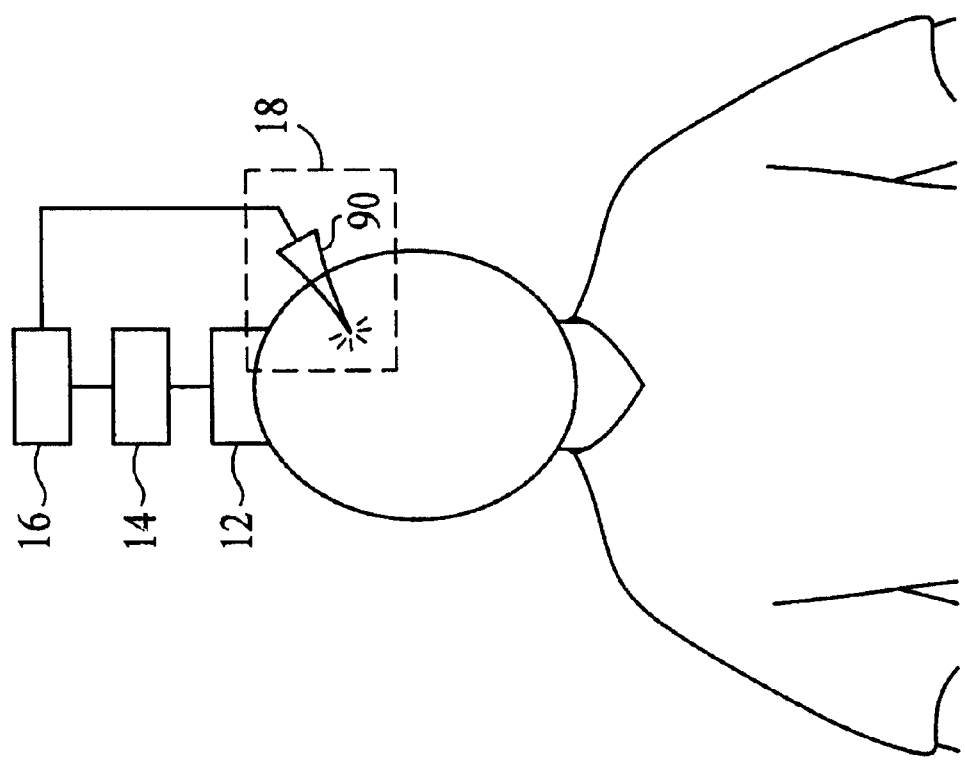
FIG. 15 shows a balance prosthesis in which the stimulator is an electrode implanted proximate to the wearer's inner ear.

In one embodiment of the balance prosthesis 10, the display provides sensory replacement. In this case, the stimulator 18 provides information to the wearer using the same pathways as the those used by a healthy vestibular system for transmission of endogenous feedback signals. FIG. 15 and its accompanying discussion describe one example of an embodiment in which the stimulator 18 and the encoder 16 cooperate to provide sensory replacement.

Figure 8:
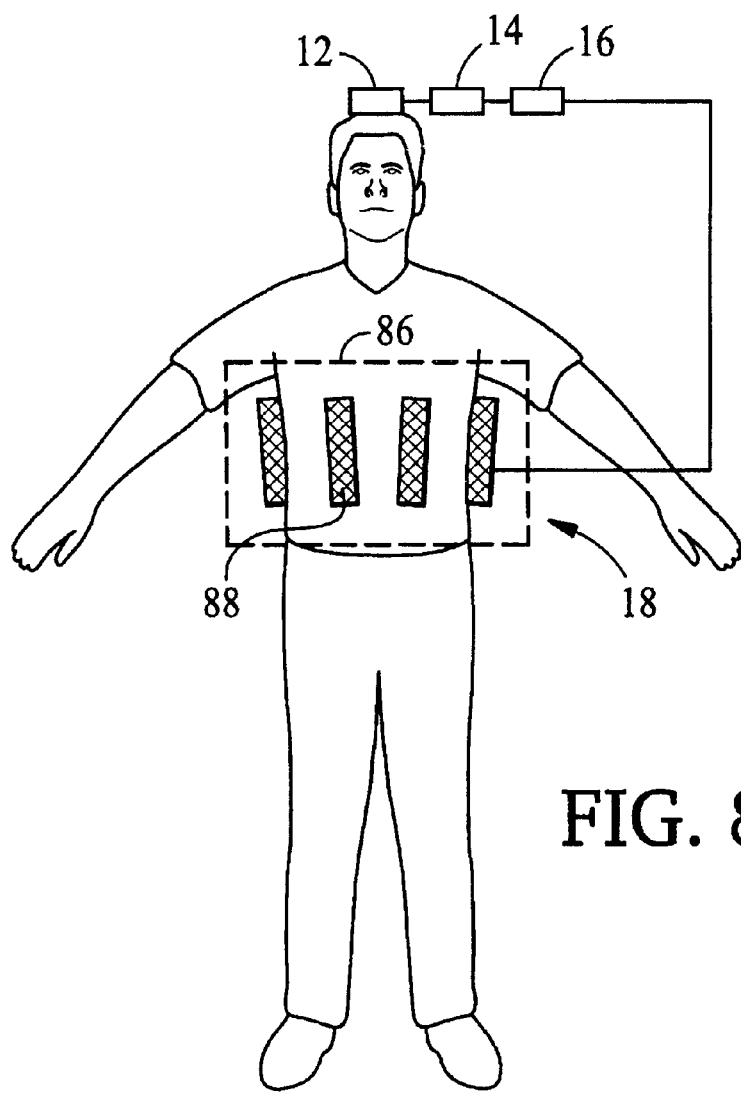
FIG. 8 shows a stimulator having a tactor set worn on the wearer's skin.

In another embodiment of the balance prosthesis 10, an example of which is described in connection with FIG. 8, the display provides sensory substitution. In this case, the stimulator 18 communicates the feedback signal to the wearer using a pathway other than those used by the healthy vestibular system.

In a balance prosthesis 10 for sensory substitution, one available pathway to the wearer's nervous system is through the wearer's sense of touch. In this embodiment, the stimulator 18 includes an array 86 of "tactors" 88 to be worn on the wearer's skin, as shown in FIG. 8. Each tactor 88 is an individually addressable electromechanical vibrating element. When energized, each tactor 88 vibrates at a frequency that is readily perceived by the wearer. A suitable frequency is one between 250 Hz and 400 Hz. Vibrating elements other than electromechanical vibrating elements can also be used. For example, a vibrating element can be purely mechanical membrane or diaphragm that is energized by pneumatic or hydraulic pressure. Alternatively, the pathway to the wearer's nervous system can be through galvanic stimulation of, for example, the tongue.

Other stimulators can be substituted or used in addition to those described above. For example, the stimulator 18 can include an acoustic transducer incorporated into a headset to provide an acoustic signal to the wearer. Alternatively, the stimulator 18 can provide a visual signal. Such a stimulator 18 can be incorporated into a pair of glasses to enable the wearer to assess spatial orientation without distraction.

The choice of which tactors 88 to energize and when to energize them depends on the manner in which the encoder 16 encodes the feedback signal.

Figure 9:
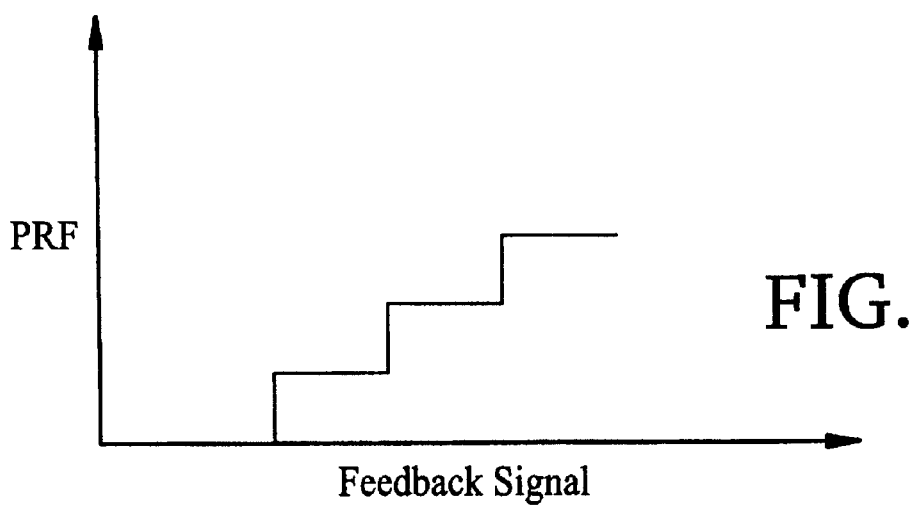
FIG. 9 shows the variation in pulse repetition frequency applied to the tactors in FIG. 8.
Figure 11:
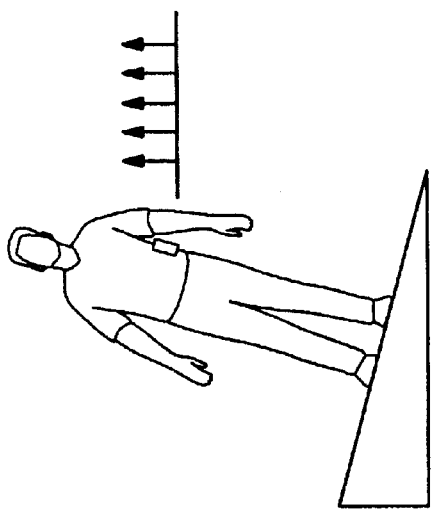
FIGS. 10–11 illustrate the indication of tilt angle through modulation of pulse repetition frequency applied to a tactor.
Figure 10:
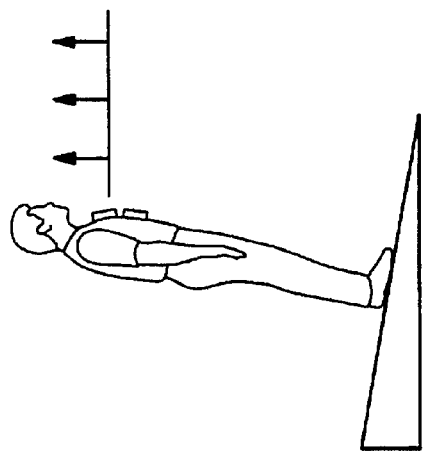

In one method of encoding the feedback signal, a tactor 88 is pulsed on and off at a pulse-repetition frequency ("PRF") that depends on the magnitude of the feedback signal. Preferably, the range of values of the feedback signal is divided into intervals, each of which corresponds to a particular PRF, as shown in FIG. 9. The specific tactors 88 that are energized provide an indication of the direction of tilt. For example, a slight ventral tilt can be indicated by energizing one or more tactors 88 on the wearer's chest at a low PRF, as shown in FIG. 10. A large lateral tilt, or alternatively, a rapid lateral tilt, can be indicated by energizing one or more tactors 88 worn on the wearer's lateral surface with a high PRF, as shown in FIG. 11.

Figure 13:
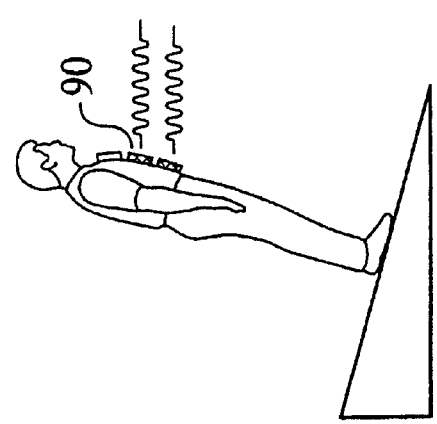
FIGS. 12–13 illustrate the indication of tilt angle through modulation of the number of tactors energized.
Figure 12:
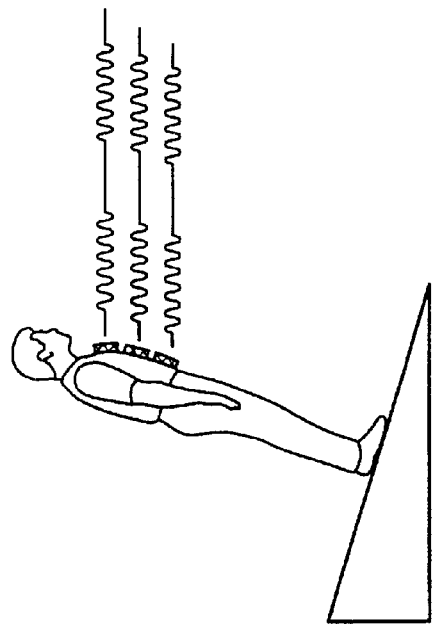

In another method of encoding the feedback signal, the value of the feedback signal at a particular instant is mapped to a particular tactor 88 or set of tactors. For example, the vibration of one tactor 88 on the wearer's chest can indicate a slight ventral tilt, as shown in FIG. 12. The vibration of several tactors 90 on the wearer's chest can indicate a larger ventral tilt or a rapid ventral tilt, as shown in FIG. 13. Dorsal and lateral tilts are indicated by vibrating one or more tactors worn on the wearer's dorsal and lateral surfaces respectively.

In a variation of the foregoing method, a column of tactors corresponds to a particular direction. The magnitude of the feedback signal in a particular direction is indicated by progressively energizing tactors on the column corresponding to that direction. When the magnitude of the feedback signal is small, only the first tactor on the tactor column is energized. When the feedback signal exceeds a threshold, the first and second tactors are energized. This pattern continues until, for sufficiently large values of the feedback signal, all the tactors in the tactor column are energized.

Figure 14:
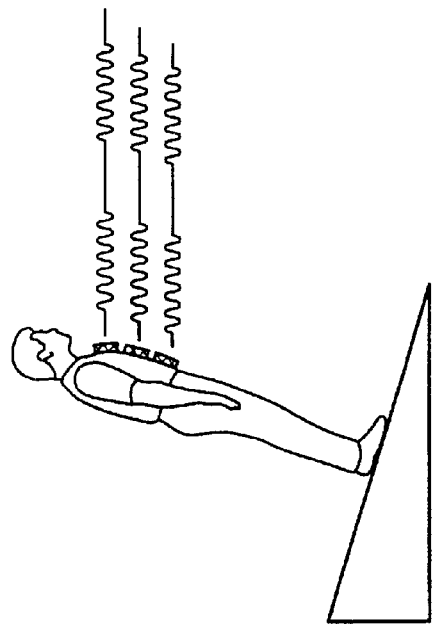
FIG. 14 illustrates the indication of tilt angle through modulation of different tactor sets at different times.

In a third method of encoding the feedback signal, illustrated in FIG. 14, the tactors 88 are energized so as to provide the sensation of waves propagating on the skin. This is analogous to the sensation experienced by a wading fisherman who senses a stream's speed and direction from the sensation of water rushing past his leg. In this method, the velocity of wave propagation can be made to indicate the magnitude of the feedback signal and the direction of wave propagation can indicate the direction of tilt. The pattern in which the tactors 88 are activated can have gaps between activated tactors 88. The pattern can also be made up of two or more underlying patterns that activate neighboring tactors 88 simultaneously.

In an alternative embodiment, shown in FIG. 15, the pathway to the wearer's nervous system is directly through one of the nerves used by a properly functioning vestibular system. In this embodiment, the stimulator 18 includes one or more transmitting electrodes 90 that are to be implanted into the wearer so as to be in electrical communication with a nerve. The transmitting electrodes 90 can be implanted in or near, for example: the sensory epithelium of the vestibular end organs; the nerve fiber bundles that separately serve each one of the five end organs in each inner ear; the vestibular branch of the eighth nerve, or Scarpa's ganglion; the vestibular nuclei of the brain stem; any other portion of the central nervous system through which it is possible to elicit a vestibular response, reflex, or sensation; or on the surface of the skin near one or more of the foregoing stimulation sites.

The signal provided to the transmitting electrodes 90 depends on the method used by the encoder 16 to encode the feedback signal. In one encoding method, the encoder 16 modulates a baseline PRF in a manner that indicates the value of the feedback signal. For example, the encoder 16 may increase a baseline PRF when the head rotates to the right and decrease when the head rotates to the left. In another encoding method, the encoder 16 can decrease or increase an applied voltage in response to the value of the feedback signal. For example, the encoder 16 can increase an applied voltage over a baseline value when the head rotates to the right and decrease the applied voltage to below the baseline value when the head rotates to the left. This type of encoding is analogous to amplitude modulation. Alternatively, in response to the position of the head, the encoder 16 can increase or decrease the frequency of a waveform relative to a baseline frequency. This type of encoding is analogous to frequency modulation.

Another encoding method exploits stochastic resonance by introducing a small amount of noise into the transmitting electrodes 90. This noise is selected to enhance sensitivity to neural stimulation. The noise introduced into the transmitting electrodes 90 can cause stochastic variation in a baseline amplitude or stochastic variation in a baseline pulse repetition frequency of the nerve into which the transmitting electrodes 90 are introduced.

Figure 16:
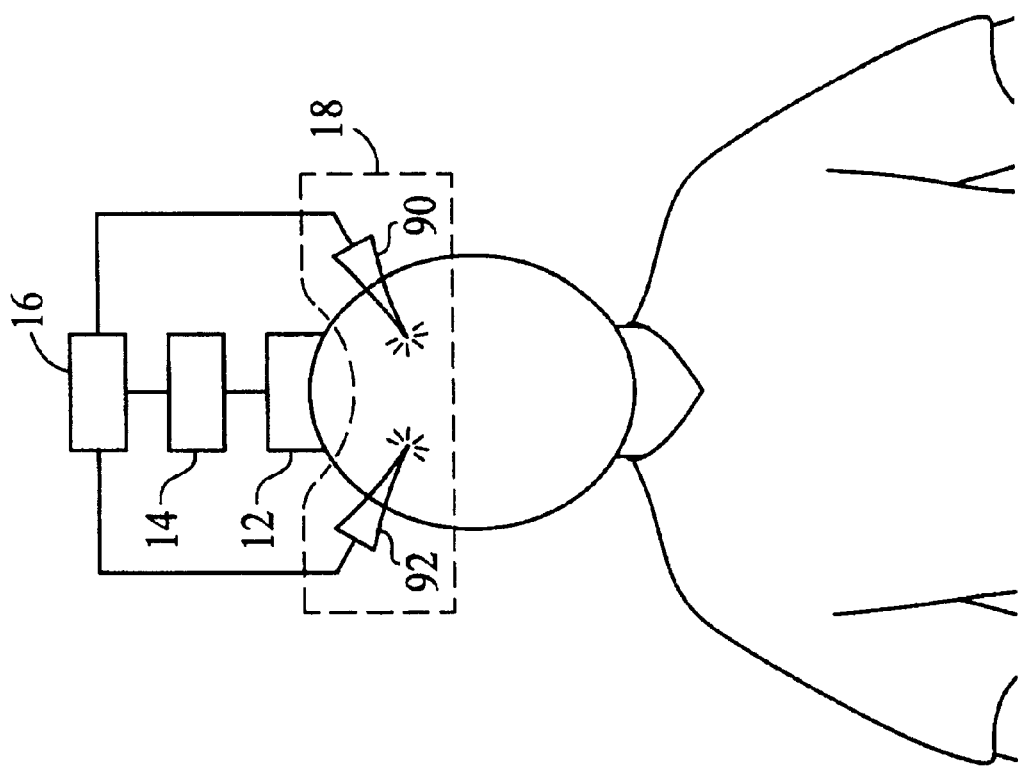
FIG. 16 shows a balance prosthesis in which the stimulator is an electrode implanted adjacent to each of the wearer's inner ears.

A normal human being has two vestibular systems, one in each inner ear that cooperate to provide balance information to the central nervous system. In a bilateral embodiment, shown in FIG. 16, the balance prosthesis 10 simulates the cooperation of the two vestibular systems by providing two transmitting electrodes. The bilateral embodiment includes a first transmitting electrode 90 implanted to stimulate a first neural pathway and a second transmitting electrode 92 implanted to stimulate a second neural pathway. The first and second neural pathways are normally used to transmit endogenous feedback signals. In response to a head rotation, the encoder 16 increases the PRF of the signal applied to the first transmitting electrode 90 while simultaneously decreasing the PRF of the signal applied to the second transmitting electrode 92. Alternatively, in response to a head rotation, the encoder 16 could increase a voltage level applied to the first transmitting electrode 90 while simultaneously decreasing that applied to the second transmitting electrode 92.

In some vestibular disorders, the difficulty arises not because the vestibular system fails to send a signal but because the vestibular system sends an incorrect signal. For example, in Meniere's disease, the vestibular system sends a signal indicating motion even when no motion has in fact occurred. To accommodate vestibular disorders of this type, one embodiment of the balance prosthesis 10 includes a transmitting electrode 90 and a receiving electrode 94, both of which are implanted into a neural pathway used by the offending vestibular system, as shown in FIG. 17.

Figure 17:
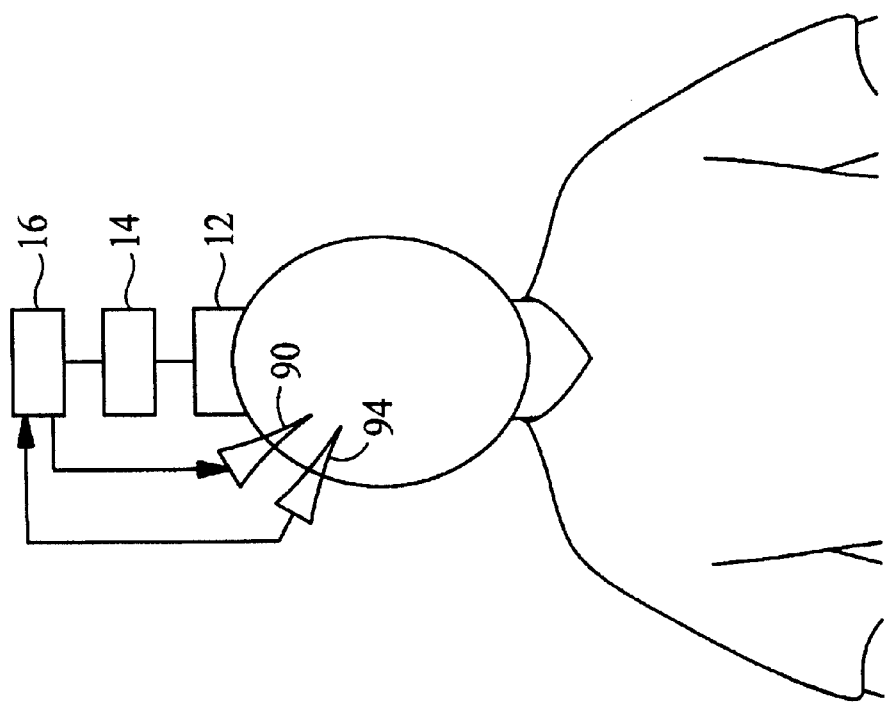
FIG. 17 shows the balance prosthesis of FIG. 15 with the addition of a sensing electrode to detect endogenous signals generated by the wearer's vestibular system.

In the balance prosthesis 10 shown in FIG. 17, the receiving electrode 94 detects the endogenous signal generated by the offending vestibular system and provides it to the encoder 16. The encoder 16 compares the endogenous signal with the estimate of the wearer's motion as provided by the digital signal processor 14. If the endogenous signal is consistent with the output of the digital signal processor 14, the encoder 16 does nothing further and the wearer uses the endogenous signal as a basis for maintaining balance. However, if the endogenous signal is inconsistent with the estimate of the wearer's motion as provided by the digital signal processor 14, the encoder 16 applies a signal to the transmitting electrode 90 that is selected to both cancel the endogenous signal and to generate a replacement signal that embodies the estimate of the motion as provided by the digital signal processor 14.

Figure 18:
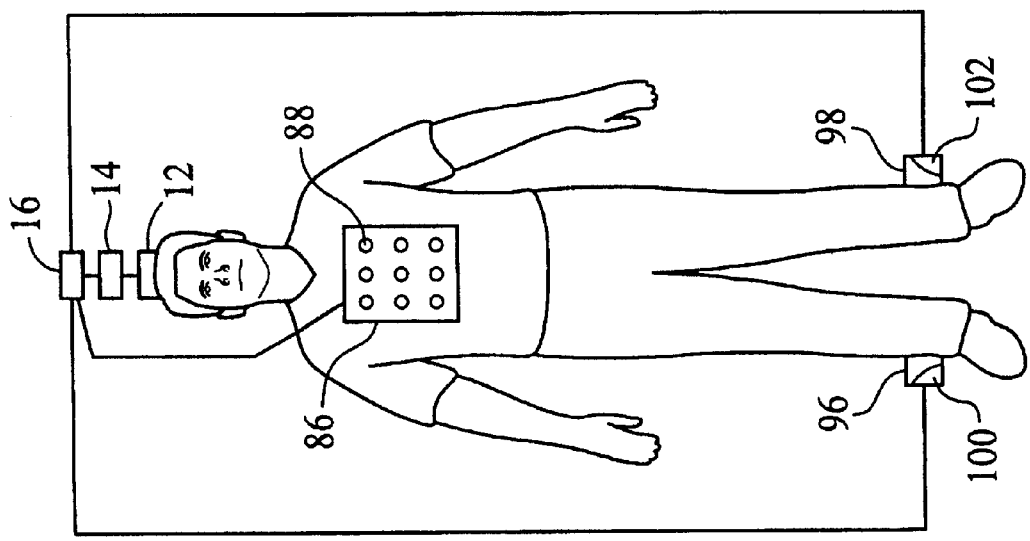
FIG. 18 shows a balance prosthesis having additional motion sensing systems mounted on different body parts of the wearer.

In another embodiment of the balance prosthesis 10, shown in FIG. 18, the encoder 16 communicates the same tilt to the wearer in different ways depending on the positions of body parts relative to each other or relative to the inertial coordinate system. The usefulness of this feature is apparent from observing that when one stands with one's feet side by side and far apart from each other, even a large lateral tilt fails to threaten one's stability. However, given the same stance, even a small ventral or dorsal tilt undermines one's stability. It is therefore desirable to more assertively draw the wearer's attention to a tilt when that tilt is a dorsal or ventral tilt and to draw less attention to the same tilt when it is a lateral tilt.

The illustrated balance prosthesis 10 includes one or more additional motion sensing systems 96, 98 and associated digital signal processors 100, 102 that can be mounted on additional body parts of the wearer. The associated digital signal processors 100, 102 are in data communication with the encoder 16.

Each digital signal processor 100, 102 generates an estimate of the position of the body part on which its associated motion sensing system 96, 98 is mounted. The digital signal processors 100, 102 then provide these estimates to the encoder 16, which then incorporates them into the signal provided to the stimulator 18.

Figure 19:
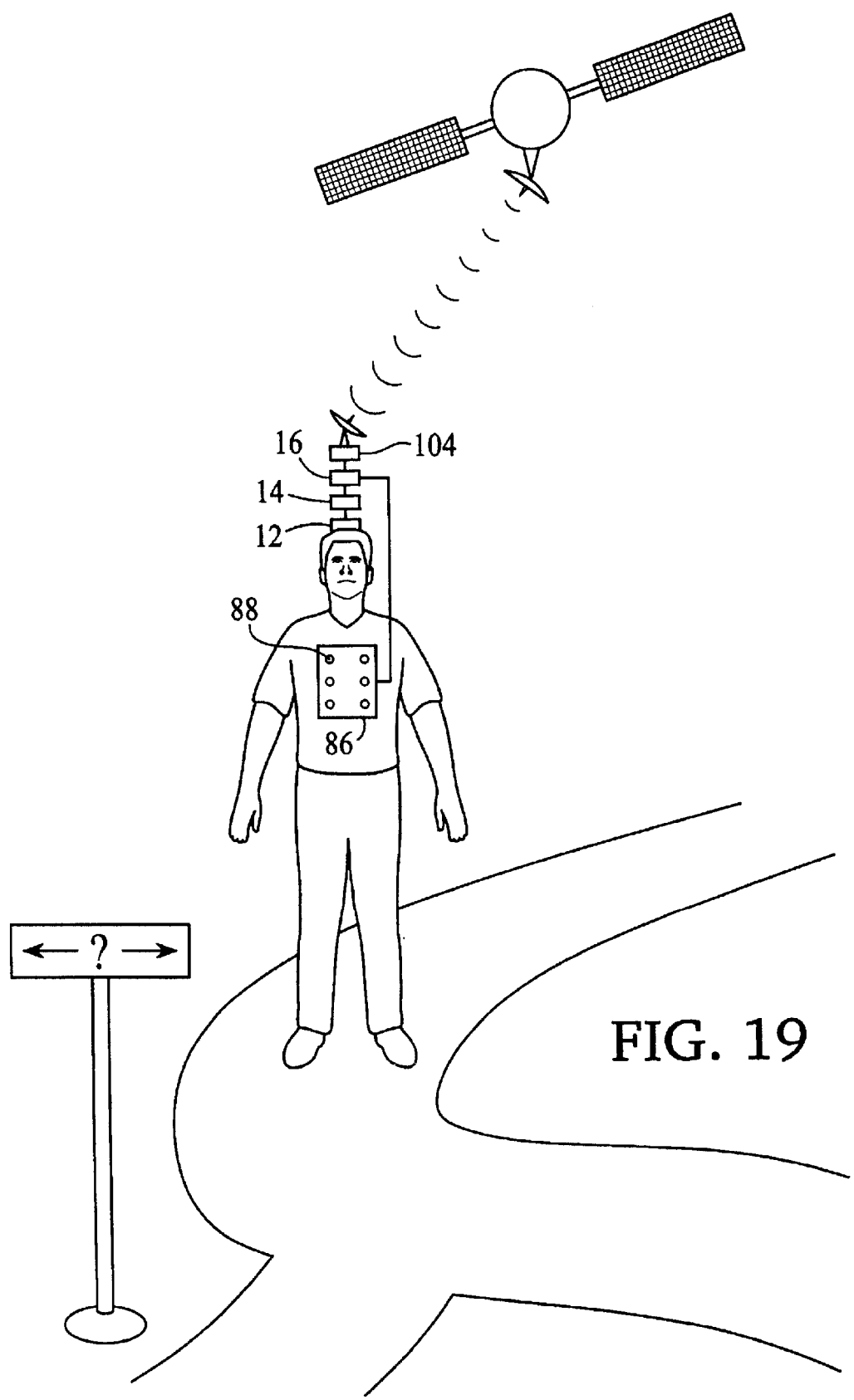
FIG. 19 shows a balance prosthesis equipped with a receiver.

As suggested by FIG. 18, the encoder 16 can use information other than the motion signal to generate the feedback signal. In the example of FIG. 18, this additional information is derived from motion sensing systems 96, 98 located on other parts of the body. However, the additional information can be derived from any source. For example, in an alternative embodiment shown in FIG. 19, a receiver 104 provides to the encoder 16 a location signal indicative of the wearer's location. Such a location signal can be derived from a GPS signal when the receiver 104 is a GPS receiver. The encoder 16 uses location data provided by the receiver 104 and the output of the digital signal processor 14 to select an optimal path to a desired location and to guide the wearer along that path. In this embodiment, the tactors 88 on one side of the wearer vibrate whenever the wearer strays from the optimal path in the direction corresponding to that side.

Alternatively, a spacecraft or a submarine could be equipped with short-range transmitters that broadcast a signal indicative of their location. The receiver 104 could then receive these signals and provide location information to the encoder 16 to enable the encoder 16. The encoder 16 could then generate a tactile signal that would a assist crew member wearing the balance prosthesis 10 in evacuating the vessel, even under conditions of reduced visibility.

The encoder 16 can be configured to generate a feedback signal on the basis of the estimate provided by the digital signal processor 14 and one or more additional signals. In the foregoing examples, the additional signals are signals that provide information concerning the location of the wearer and information concerning the location of one or more body parts of the wearer. However, the information provided by the additional signals is not limited to these examples. Other examples of information that can be provided by the additional signals include tactile pressure or joint angle measurements from other body parts.

Even a healthy vestibular system is unable to detect certain types of acceleration. For example, a seasoned pilot on a commercial airliner can execute a turn so gracefully that the passengers remain unaware of the turn. This is because the frequency response of the human vestibular system has a low-frequency cut-off below which accelerations become imperceptible. Similarly, high-frequency vibrations can be imperceptible because of a similar high-frequency cut-off of the human vestibular system. The human vestibular system therefore functions like a bandpass filter having a pass band dictated by the structures of the various accelerometers that make up the system.

In an alternative embodiment, the balance prosthesis 10 can function as a sensory enhancer for extending the wearer's range of sensitivity to acceleration. In this embodiment, the encoder 16 generates a feedback signal that is zero when the motion would be detectable by the vestibular system and non-zero when the motion would otherwise be undetectable by the wearer's vestibular system.

Having described the invention, and a preferred embodiment thereof, what we claim as new, and secured by letters patent is:

What is claimed is:

1. An apparatus for providing a wearer with information indicative of spatial orientation of a body part of said wearer, said apparatus comprising:

a motion sensing system to be worn by a wearer, said motion sensing system generating a motion signal indicative of motion experienced by said body part of said wearer;

a signal processor in communication with said motion sensing system for generating an estimate of said spatial orientation of said body part on the basis of said motion signal;

a stimulator configured to provide a signal to a nervous system of said wearer in response to a feedback signal, said stimulator including an electrode adapted to be inserted proximate to a nerve in said wearer; and an encoder in communication with said signal processor and said electrode, said encoder configured to generate said feedback signal on the basis of said estimate of said spatial orientation and to introduce noise into said electrode, said noise being selected to enhance sensitivity of said nerve to a signal indicative of spatial orientation.

2. An apparatus for providing a wearer with information indicative of spatial orientation of a body part of said wearer, said apparatus comprising:

a motion sensing system to be worn by a wearer, said motion sensing system generating a motion signal indicative of motion experienced by said body part of said wearer;

a signal processor in communication with said motion sensing system for generating an estimate of said spatial orientation of said body part on the basis of said motion signal;

a stimulator including
a transmitting electrode adapted to be inserted proximate to a nerve in said wearer and configured to provide a signal to a nervous system of said wearer in response to a feedback signal, and
a measurement electrode in communication with said encoder for detecting an endogenous signal in said nerve; and an encoder in communication with said signal processor, said transmitting electrode and said measurement electrode, said encoder being configured to generate said feedback signal on the basis of said endogenous signal and said estimate of said spatial orientation.

3. An apparatus for providing a wearer with information indicative of spatial orientation of a body part of said wearer, said apparatus comprising:

a motion sensing system to be worn by said wearer, said motion sensing system including a micro-mechanical rotation sensor configured to generate a motion signal that includes information indicative of rotational motion experienced by said wearer;

a signal processor in communication with said motion sensing system for generating an estimate of said spatial orientation of said body part on the basis of said motion signal;

an encoder in communication with said signal processor, said encoder configured to generate a feedback signal on the basis of said estimate of said spatial orientation; and a stimulator responsive to said feedback signal from said encoder, said stimulator configured to provide a signal to a nervous system of said wearer in response to said feedback signal.

4. The apparatus of claim 3, wherein said micro-mechanical rotation sensor comprises a micro-mechanical device having a proof mass that undergoes a periodic motion susceptible to disturbance by a rotational motion.

5. The apparatus of claim 4, wherein said micro-mechanical device includes a tuning fork having a tine integrated with said proof mass, and a capacitor coupled to said proof mass, said capacitor having a capacitance that depends on a position of said proof mass relative to said capacitor.

6. An apparatus for providing a wearer with information indicative of spatial orientation of a body part of said wearer, said apparatus comprising:

a motion sensing system to be worn by a wearer, said motion sensing system including a micro-mechanical translation sensor configured to generate a motion signal that includes information indicative of linear acceleration experienced by said wearer;

a signal processor in communication with said motion sensing system for generating an estimate of said spatial orientation of said body part on the basis of said motion signal;

an encoder in communication with said signal processor, said encoder configured to generate a feedback signal on the basis of said estimate of said spatial orientation; and a stimulator responsive to said feedback signal from said encoder, said stimulator configured to provide a signal to a nervous system of said wearer in response to said feedback signal.

7. The apparatus of claim 6, wherein said micro-mechanical translation sensor comprises a micro-mechanical device having a proof mass, said proof mass having a position susceptible to displacement from an equilibrium position by a linear acceleration.

8. The apparatus of claim 7, wherein said micro-mechanical device includes a cantilevered beam having a proof mass integrated onto a distal end, said proof mass being coupled to a capacitor, said capacitor having a capacitance that depends on a position of said proof mass relative to said capacitor.

9. An apparatus for providing a wearer with information indicative of spatial orientation of a body part of said wearer, said apparatus comprising:

a motion sensing system to be worn by a wearer, said motion sensing system generating a motion signal indicative of motion experienced by said body part of said wearer;

a signal processor in communication with said motion sensing system for generating an estimate of said spatial orientation of said body part on the basis of said motion signal, said signal processing system being configured to resolve said estimate into at least a component arising from linear acceleration due to gravity and a component arising from linear acceleration resulting in translation;

an encoder in communication with said signal processor, said encoder configured to generate a feedback signal on the basis of said estimate of said spatial orientation; and a stimulator responsive to said feedback signal from said encoder, said stimulator configured to provide a signal to a nervous system of said wearer in response to said feedback signal.

10. The apparatus of claim 9, wherein said signal processing system comprises a low-pass filter to filter a first inertial guidance signal and a high-pass filter to filter a second inertial guidance signal, said low-pass filter and said high-pass filter having complementary filter transfer functions.

11. The apparatus of claim 9, wherein said signal processing system is configured to determine a current direction of a gravity vector on the basis of an information provided by said motion sensing system and to remove the effect of said gravity vector from a translation sensor output.

12. The apparatus of claim 9, wherein the signal processing system comprises a low-pass filter and a high-pass filter, the low-pass filter and the high-pass filter being configured to distinguish between linear acceleration and acceleration due to gravity.

13. The apparatus of claim 9, wherein the signal processing system is configured to distinguish between linear acceleration and acceleration due to gravity on the basis of rotational cues.

14. The apparatus of claim 9, wherein the signal processing system comprises a Kalman filter.

15. The apparatus of claim 9, wherein the signal processing system comprises a filter other than a Kalman filter.

16. An apparatus for providing a wearer with information indicative of spatial orientation of a body part of said wearer, said apparatus comprising:

- a motion sensing system to be worn by a wearer, said motion sensing system generating a motion signal indicative of motion experienced by said body part of said wearer;
- a signal processor in communication with said motion sensing system for generating an estimate of said spatial orientation of said body part on the basis of said motion signal;
- a GPS receiver to be worn by the wearer;
- an encoder in communication with said signal processor and with said receiver, said encoder configured to generate a feedback signal on the basis of said estimate of said spatial orientation and an additional signal from said receiver; and
- a stimulator responsive to said feedback signal from said encoder, said stimulator configured to provide a signal to a nervous system of said wearer in response to said feedback signal.

17. An apparatus for providing a wearer with information indicative of spatial orientation of a body part of said wearer, said apparatus comprising:

- a motion sensing system to be worn by a wearer, said motion sensing system generating a motion signal indicative of motion experienced by said body part of said wearer;
- a signal processor in communication with said motion sensing system for generating an estimate of said spatial orientation of said body part on the basis of said motion signal;
- a receiver to be worn by the wearer, said receiver being adapted to detect a signal indicative of a quantity selected from a group consisting of a joint angle measurement, a tactile pressure, a location of said wearer, and a location of a body part of said wearer
- an encoder in communication with said signal processor and with said receiver, said encoder configured to generate a feedback signal on the basis of said estimate of said spatial orientation and an additional signal from said receiver; and
- a stimulator responsive to said feedback signal from said encoder, said stimulator configured to provide a signal to a nervous system of said wearer in response to said feedback signal.

* * * * *